United States Patent
Yano et al.

(10) Patent No.: US 7,541,467 B2
(45) Date of Patent: Jun. 2, 2009

(54) FLUORESCENT ZINC ION SENSOR

(75) Inventors: Shigenobu Yano, 6-7-45-108, Ayameikeminami, Nara-shi, Nara 631-0033 (JP); Yuji Mikata, 4-6-5-2, Kunimidai, Kizu-cho, Soraku-gun, Kyoto 619-0216 (JP)

(73) Assignees: Shigenobu Yano, Nara (JP); Yuji Mikata, Kyoto (JP); Sekisui Medical Co., Ltd., Tokyo (JP)

( * ) Notice: Subject to any disclaimer, the term of this patent is extended or adjusted under 35 U.S.C. 154(b) by 300 days.

(21) Appl. No.: 10/902,432

(22) Filed: Jul. 30, 2004

(65) Prior Publication Data

US 2005/0182253 A1 Aug. 18, 2005

(30) Foreign Application Priority Data

Jan. 9, 2004 (JP) ............................. 2004-003707

(51) Int. Cl.
- C07D 215/20 (2006.01)
- C07F 3/06 (2006.01)
- C09K 11/54 (2006.01)

(52) U.S. Cl. .................. 546/177; 546/10; 546/140; 546/176; 252/301.6 R

(58) Field of Classification Search ............. 546/2, 546/140, 176, 177, 10; 252/301.6 P
See application file for complete search history.

(56) References Cited

U.S. PATENT DOCUMENTS

| | | | |
|---|---|---|---|
| 4,891,075 A | 1/1990 | Dakubu et al. | |
| 4,968,631 A | 11/1990 | Dakubu | |
| 5,037,615 A | 8/1991 | Kane | |
| 5,049,673 A | 9/1991 | Tsien et al. | |
| 5,208,148 A | 5/1993 | Haugland et al. | |
| 5,246,867 A | 9/1993 | Lakowiez et al. | |
| 5,302,731 A | 4/1994 | Pitner et al. | |
| 5,340,716 A | 8/1994 | Ullman et al. | |
| 5,380,880 A | 1/1995 | Pitner et al. | |
| 5,393,514 A | 2/1995 | Pitner et al. | |
| 5,451,343 A | 9/1995 | Neckers et al. | |
| 5,622,821 A | 4/1997 | Selvin et al. | |
| 5,623,080 A | 4/1997 | Neckers et al. | |
| 5,639,615 A | 6/1997 | Selvin et al. | |
| 5,648,270 A | 7/1997 | Kuhn et al. | |
| 5,656,433 A | 8/1997 | Selvin et al. | |
| 5,800,996 A | 9/1998 | Lee et al. | |
| 5,863,727 A | 1/1999 | Lee et al. | |
| 5,874,590 A | 2/1999 | Nagano et al. | |
| 6,013,802 A | 1/2000 | Hoyland et al. | |
| 6,201,134 B1 | 3/2001 | Nagano et al. | |
| 6,403,625 B1 | 6/2002 | Nagao et al. | |
| 6,441,197 B1 | 8/2002 | Nagano et al. | |
| 6,469,051 B2 | 10/2002 | Nagano et al. | |
| 6,525,088 B1 | 2/2003 | Nagano et al. | |
| 6,569,892 B2 | 5/2003 | Nagano et al. | |
| 6,656,927 B1 | 12/2003 | Nagano et al. | |
| 6,753,156 B1 | 6/2004 | Mathis et al. | |
| 6,756,231 B1 | 6/2004 | Nagano et al. | |
| 6,833,386 B2 | 12/2004 | Nagano et al. | |
| 6,903,226 B2 | 6/2005 | Nagano et al. | |
| 6,936,687 B1 | 8/2005 | Komoriya et al. | |
| 6,972,182 B1 | 12/2005 | Colyer et al. | |
| 2002/0177120 A1 | 11/2002 | Elliott et al. | |
| 2003/0153027 A1 | 8/2003 | Nagano et al. | |
| 2003/0157727 A1 | 8/2003 | Nagano et al. | |
| 2003/0162298 A1 | 8/2003 | Nagano et al. | |
| 2004/0043498 A1 | 3/2004 | Nagano et al. | |
| 2004/0147035 A1 | 7/2004 | Nagano et al. | |
| 2005/0037332 A1 | 2/2005 | Komatsu et al. | |
| 2005/0064308 A1 | 3/2005 | Nagano et al. | |
| 2005/0123478 A1 | 6/2005 | Nagano et al. | |
| 2005/0130314 A1 | 6/2005 | Nagano et al. | |
| 2005/0182253 A1 | 8/2005 | Yano et al. | |
| 2006/0030054 A1 | 2/2006 | Nagano et al. | |

FOREIGN PATENT DOCUMENTS

| | | |
|---|---|---|
| EP | 0314480 | 5/1989 |
| EP | 0515133 | 11/1992 |
| EP | 0582836 | 2/1994 |

(Continued)

OTHER PUBLICATIONS

Anderegg et al., Helvetica Chimica Acta, Vo.. 50, pp. 2330-2333 (1967).

(Continued)

*Primary Examiner*—Charanjit S Aulakh
(74) *Attorney, Agent, or Firm*—Greenblum & Bernstein, P.L.C.

(57) ABSTRACT

A compound represented by the following general formula (I) or a salt thereof:

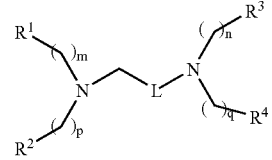

wherein $R^1$, $R^2$, $R^3$, and $R^4$ independently represent 2-quinolyl group which may be substituted, 1-isoquinolyl group which may be substituted, or 3-isoquinolyl group which may be substituted; m, n, p, and q independently represent 1 or 2; and L represents a single bond, or an alkylene group having 1 to 5 carbon atoms wherein said alkylene group may contain one or more heteroatoms in the main chain, and may have one or more substituents on the main chain, which is useful as a fluorescent zinc ion sensor.

8 Claims, 5 Drawing Sheets

FOREIGN PATENT DOCUMENTS

| | | |
|---|---|---|
| EP | 1069121 | 1/2001 |
| EP | 1260508 | 11/2002 |
| EP | 1260510 | 11/2002 |
| JP | 60-54381 | 3/1985 |
| JP | 6-207112 | 7/1994 |
| JP | 06-211831 | 8/1994 |
| JP | 08-271430 | 10/1996 |
| JP | 9-101262 | 4/1997 |
| JP | 10-88124 | 4/1998 |
| JP | 10-226688 | 8/1998 |
| JP | 5-180773 | 7/1999 |
| JP | 2000-111480 | 4/2000 |
| JP | 2000-239272 | 5/2000 |
| WO | 89/09408 | 10/1989 |
| WO | 96/42016 | 12/1996 |
| WO | 98/15830 | 4/1998 |
| WO | 99/15896 | 4/1999 |
| WO | 99/51586 | 10/1999 |
| WO | 00/00819 | 1/2000 |
| WO | 01/62755 | 8/2001 |
| WO | 01/63265 | 8/2001 |
| WO | 01/64664 | 9/2001 |
| WO | 2004/040296 | 5/2004 |
| WO | 2005/024049 | 3/2005 |

OTHER PUBLICATIONS

T. Hirano et al., "Highly Zinc-Selective Fluorescent Sensor Molecules Suitable for Biological Applications," Journal of the American Chemical Society, vol. 122, No. 49, pp. 12399-12400 (2000).

R.P. Haugland, "Handbook of Fluorescent probes and Research Products," 9th Edition Supplement, Chapter 20, pp. 805-817 (2002).

G.K. Walkup et al., "A New Cell-Permeable Fluorescent Probe for $Zn^{2+}$," Journal of the American Chemical Society, vol. 122, No. 23, pp. 5644-5645 (2000).

J. Kawakami et al., "*Ab initio* Molecular Orbital Study of Emission Mechanism of 2,6-Bis (quinolinecarboxy) methylpyridine as Fluorescent Chemosensors for Zinc and Cadmium Ions," Journal of Computer Chemistry, Japan, vol. 2, No. 2, pp. 57-62 (2003).

C.J. Frederickson et al., "A quinoline fluorescence method for visualizing and assaying the histochemically reactive zinc (bouton zinc) in the brain," Journal of Neuroscience Methods, vol. 20, pp. 91-103 (1987).

D. Zalewski et al., "Correleation of apoptosis with change in intracellular labile Zn(II) using Zinquin[(2-methyl-8-*p*-toluenesulphonamido-6-quinolyloxy)acetic acid], a new specific fluorescent probe for Zn(II)," Biochemical Journal, vol. 296, Part 2, pp. 403-408 (1993).

Reyes, J.G., et al., Biol. Res., 27, pp. 49-56, 1994.
Tsuda, M., et al., Neurosci., 17, pp. 6678-6684, 1997.
Koike, T., et al., J. Am. Chem. Soc., 118, pp. 12696-12703, 1996;
Saibou Kougaku (Cell Technology), 17, pp. 584-595, 1998.
Tanpakushitsu.Kakusan.Kouso (Protein, Nucleic Acid and Enzyme), extra No., 42, pp. 171-176, 1997.
Tetsuji Kametani, Nankodo Co., Ltd., pp. 214-215, 1997.
Handbook of Fluorescent Probes and Research Chemicals, 6th Edition by Richard P. Haugland, pp. 503 and 531-540.
Protective Groups in Organic Synthesis, T. W. Greene, John Wiley & Sons, Inc. pp. v-xxi and 369-405.
Angew. Chem., Int. Ed. (1999), 38(21), pp. 3209-3212.
Anal. Chem. (1998), 70(13), pp. 2446-2453.
Bioorganic & Medicinal Chemistry, vol. 4, No. 6, pp. 901-916, (1996).
Bioorg. Khim. (1995), 21(10), pp. 795-801.
Sci. China, Ser. B: Chem. (1998), 41(5), pp. 549-555.
J. Am. Chem. Soc. (1996), 118, pp. 6514-6515.
Hirano T. et al., "Highly Zinc-Selective Fluorescent Sensor Molecules Suitable for Biological Applications", J. Am. Chem. Soc., vol. 122, No. 49, Dec. 13, 2000, pp. 12399-12400.

Walkup G. K. et al., "A New Cell-Permeable Fluorescent Probe for $Zn^{2+}$", J. Am. Chem. Soc., vol. 122, No. 23, Jun. 14, 2000, pp. 5644-5645.

Bambot, S.B. et al., "Potential Applications of Lifetime-Based, Phase-Modulation Fluorimetry in Bioprocess and Clinical Monitoring", Trends in Biotechnology, vol. 13, No. 3, Mar. 1995, pp. 106-115, XP 004207135.

Sipior, J. et al., "Lifetime-Based Optical Sensing of pH Using Resonance Energy Transfer in Sol-Gel Films", Sensors and Actuators B; vol. 22, No. 3, Dec. 1994, pp. 181-188, XP004011062.

Selvin, P.R. et al., "Luminescence Energy Transfer Using a Terbium Chelate:Improvements on Fluorescence Energy Transfer", Proceedings of the National Academy of Science of USA, National Academy of Science, Washington, DC, US, vol. 91, Oct. 1994, pp. 10024-10028, XP001018013.

Yuan, J. et al., "Functionalization of Fluorescent Lanthanide Complexes and Their Applications to Biotechnology", Bunseki Kagaku—Japan Analyst; vol. 48, No. 12, pp. 1077-1083 (1999), XP002932633.

Rogers, M. V., Drug Discovery Today, vol. 2, pp. 156-160, 1997.
Selvin, P. R., et al., J. Am. Chem. Soc., vol. 117, pp. 8132-8138, 1995.
Stryer, L., Ann. Rev. Biochem., vol. 47, pp. 819-846, 1978.
Hemmilä, I., Drug Discovery Today, vol. 2, pp. 373-381, 1997.
New Apoptosis Experimental Protocol, 2nd ed., Yodosha, pp. 201-204, 1999.
Selvin, P. R., et al., J. Am. Chem. Soc., vol. 116, pp. 6029-6030, 1994.
J. Burch, "The Inhibition of Horse-Liver Esterase by Rhodamine B," Biochemical Journal, vol. 59, pp. 97-110 (1955).

D.D. Thomas et al., "Flourescence energy transfer in the rapid-diffusion limit," Proceedings of the National Academy of Sciences of the United States of America, vol. 75, No. 12, pp. 5746-5750 (1978).

S.M. Yeh et al., "Characterization of Transferin Metal-Binding Sites by Diffusion-Enhanced Energy Transfer," Biochemistry, 19, pp. 5057-5062 (1980).

R.A. Edwards et al., "Spectroscopic Studies of Cibacron Blue and Congo Red Bound to Dehydrogenases and Kinases. Evaluation of Dyes as Probes of the Dinucleotide Fold," Biochemistry, vol. 18, No. 23, pp. 5197-5204 (1979).

C.F. Meares et al., "Diffusion-Enhanced Energy Transfer Shows Accessibility of Ribonucleic Acid Polymerase inhibitor Binding Sites," Biochemistry, 20, pp. 610-617 (1981).

T.G. Wensel et al., "Electrostatic Properties of Myoglobin Probed by Diffusion-Enhanced Energy Transfer," Biochemistry, 22, pp. 6247-6254 (1983).

M.M. Federici et al., "Interaction of Cibacron Blue $F_3GA$ with Glutamine Synthetase: Use of the Dye as a Conformational Probe. 1. Studies Using Unfractionated Dye Samples," Biochemistry, 24, pp. 647-660 (1985).

T.G. Wensel et al., "Diffusion-Enhanced Lanthanide Energy-Transfer Study of DNA-Bound Cobalt(III) Bleomycins: Comparisons of Accessibility and Electrostatic Potential with DNA Complexes of Ethidium and Acridine Orange," Biochemistry, 24, pp. 3060-3069 (1985).

B.S. Isaacs et al., "A Domain of Membrane-Bound Coagulation Factor Va Is Located Far from the Phospholipid Surface. A Fluorescence Energy Transfer Measurement," Biochemistry, 25, pp. 4958-5969 (1986).

T.G. Wensel et al., "Study of Biological Macromolecules by Diffusion-Enhanced Lanthanide Energy Transfer," Journal of the Less-Common Metals, 149, pp. 143-160 (1989).

P.R. Selvin et al., "Luminescence Resonance Energy Transfer," Journal of the American Chemical Society, 116, pp. 6029-6030 (1994).

T. Yamamoto et al., "Determination of Electrostatic Potential Around Specific Locations on the Surface of Actin by Diffusion-enhanced Fluorescence Resonance Energy Transfer," Journal of Molecular Biology, 241, pp. 714-731 (1994).

S.C.J. Meskers et al., "Analysis of Delayed Luminescence from Some Quenchers of $Tb(DPA)_3^{3-}$ Emission: Proof for an Energy Transfer Quenching Mechanism," Journal of Alloys and Compounds, 250, pp. 332-335 (1997).

D.D. Root, "In situ Molecular Association of Dystrophin with Actin Revealed by Sensitized Emission Immuno-Resonance Energy Transfer," Proceedings of the National Academy of Sciences of the United States of America, 94, pp. 5685-5690 (1997).
C. Mucignat-Caretta et al., "Building of Two Fluorescent cAMP Analogues to Type I and II Regulatory Subunits of cAMP-Dependent Protein Kinases," Biochimica et Biophysica Acta, 1357, pp. 81-90 (1997).
Y.-W. Park et al., "Homogeneous Proximity Tyrosine Kinase Assays: Scintillation Proximity Assay versus Homogeneous Time-resolved Fluorescence," Analytical Biochemistry, 269, pp. 94-104 (1999).
K. Blomberg et al., "Terbium and Rhodamine as Labels in a Homogeneous Time-resolved Fluorometric Energy Transfer Assay of the β Subunit of Human Chorionic Godadotropin in Serum," Clinical Chemistry, 45, 855-861 (1999).
L.L. Pearce et al., "Role of Metallothionein in Nitric Oxide Signaling as Revealed by a Green Fluorescent Fusion Protein," Proceedings of the National Academy of Sciences of the United States of America, 97, pp. 477-382 (2000).
M. Koresawa et al., "Development of a Time-Resolved Fluorometric Detection System Using Diffusion-Enhanced Energy Transfer," Analytical Chemistry, 72, pp. 4904-4907 (2000).
T. Nagano et al., "Specific Detection Method and Useful Generating System of Singlet Oxygen," Free Radicals in Clinical Medicine, vol. 7, pp. 35-41 (1993).
I. Saito et al., "Methyl-Substituted Poly(vinylnaphthalene) as a Reversible Singlet Oxygen Carrier," J. Am. Chem. Soc., vol. 107, pp. 6329-6334, 1985.
T. W. Greene et al., "Protective Groups in Organic Synthesis," John Wiley & Sons, Inc., pp. v-xxi and 369-405 (1981).
J. Kabatc et al., "Free Radical Polymerization Initiated via Photoinduced Intermolecular Electron Transfer Process: Kinetic Study 3$^1$," Polymer 40(3), pp. 735-745 (1999).
K. Setsukinai et al., "Fluorescence Switching by O-dearylation of 7-aryloxycoumarins. Development of Novel Flourescence Probes to Detect Reactive Oxygen," J. Chem. Soc., Perkin Trans. 2, 12, pp. 2453-2457, (2000).
J.W. Firth et al., "Some Phenoxy-2H-benzo[b]pyrans," J. Chem. Research (S), vol. 2000, No. 7, pp. 308-308 (Jul. 2000).
J.G. Reyes et al., "A Fluorescence Method to Determine Picomole Amounts of Zn(II) in Biological Systems," Biol. Res., vol. 27, pp. 49-56, (1994).
M. Tsuda et al., "Expression of Zinc Transporter Gene, ZnT-1, is Induced After Transient Forebrain Ischemia in the Gerbil," The Journal of Neuroscience, vol. 17, No. 17, pp. 6678-6684 (Sep. 1, 1997).
T. Koike et al., "A Novel Biomimetic Zinc(II)—Fluorophore, Dansylamidoethyl-Pendant Macrocyclic Tetraamine 1,4,7,10-Tetraazacyclododecane (Cyclen)," J. Am. Chem. Soc., vol. 118, 1996, pp. 12696-12703.
Web site of the Pharmaceutical Society of Japan, on Feb. 1, 2003, a copy of the screenshot is enclosed. The subject matter of the screenshot was then published in an Abstract of the "The 123$^{rd}$ Annual Congress of the Pharmaceutical Society of Japan" on Mar. 5, 2003 for presentation No. 29[P1]1-219 entitled "Development of Fluorescent Probe Having Low Affinity of Zinc" in the 123$^{rd}$ Annual Congress of the Pharmaceutical Society of Japan held on Mar. 27-29, 2003.
Newport Green: A Catalog of Molecular Probes, Inc. "Handbook of Fluorescent Probes and Research Chemical, Chapter 22—Section 22.7 Fluorescent Indicators for $Zn^{2+}$ And Other Metals", 6$^{th}$ Edition by Richard P. Haugland, pp. 531-540 (1996).
Toshiaki Hiratsuka, "Tanpakushitsu-Kakusan-Kouso (Protein, Nucleic Acid and Enzyme)", vol. 42, No. 7, pp. 171-176 (1997).
L. Lindqvist et al., "Radiationless Transitions in Xanthene Dyes", J. Chem. Phys., vol. 44, pp. 1711-1712 (1966).
Richard P. Haugland, Handbook of Fluorescent Probes and Research Chemicals, Sixth Edition, Chapters 22-24, pp. 503-584 (1996).
Theodora W. Greene, Protective Groups in Organic Synthesis, Chapter 7, pp. 218-287 (1981).
Rajendra Nath Sen et al., "The Condensation of Primary Alcohols with Resorcinol and Other Hydroxy Aromatic Compounds", J. Am. Chem. Soc., vol. 47, pp. 1079-1091 (1925), XP002332482.
R. Kurduker et al., "Search for Physiologically Active Compounds", Proc. Indian. Acad. Sci. Sect. A., vol. 57, pp. 280-287 (1963).
A. Minta et al., "Fluorescent Indicators for Cytosolic Calcium Based on Rhodamine and Fluorescein Chromophores", J. Biol. Chem., vol. 264, No. 14, pp. 8171-8178 (1989).
P.K. Grover et al., "Xanthones. Part IV. A New Synthesis of Hydroxyxanthones and Hydroxybenzophenones," J. Chem. Sci. (London), pp. 3982-3985 (1955).
William A. Pryor et al., "A Practical Method for Preparing Peroxynitrite Solutions of Low Ionic Strength and Free Hydrogen Peroxide," Free Radical Biology & Medicine, vol. 18, No. 1, pp. 75-83 (1995).
Stephen L. Hempel et al., "Dihydrofluorescein Diacetate is Superior for Detecting Intracellular Oxidants: Comparison with 2',7'-Dichlorodihydrofluorescein Diacetate, 5(and 6)-Carboxy-2',7'-Dichlorodihydrofluorescein Diacetate, and Dihydrorhodamie 123," Free Radical Biology & Medicine, vol. 27, Nos. 1/2, pp. 146-159 (1999).
Joseph A. Hrabie et al., "New Nitric Oxide-Releasing Zwitterions Derived from Polyamines," J. Org. Chem. vol. 58, pp. 1472-1476 (1993).
English Language Abstract of JP 2000-239272.
English Language Abstract of JP 9-101262.
English Language Abstract of JP 10-88124.
English Language Abstract of JP 2000-111480.
English Language Abstract of JP 60-54381.
English Language Abstract of JP 08-2714430.
English Language Abstract of JP 10-226688.
English Language Abstract of JP 6-207112.
English Language Abstract of JP 06-211831.
An abstract of "Fluorescent Response of N, N, N', N'-Tetrakis (2-quinolylmethyl) alkanediamines Toward Zinc Ion": published on Aug. 1, 2003 for oral presentation in 21$^{st}$ ICP Satellite Symposium on Photochemistry and Photobiology of Complexes Including Supramolecular Systems and Coordination Compounds (Aug. 1-3, 2003), listed as P27.
An abstract "Fluorescent Response of Polyquinoline Derivatives toward Zinc Ion", Abstracts 1$^{st}$ Joint symposium on Biofunctional Chemistry and Biotechnology, Oct. 12-13, 2003, Kumamoto University, listed as 2OA-09.
Chemistry & Chemical Industry, vol. 56-9, Sep. 2003, pp. 1089, 1092 and 1107 listing abstract 2OA-09 on p. 1092.
An abstract of "Fluorescent Response of N, N, N', N'-Tetrakis (2-quinolylmethyl) alkanediamines Toward Zinc Ion", 10$^{th}$ International SPACC Symposium Nov. 25-27, 2003, listed as P17.
An abstract of "Fluorescent Response of Polyquinoline Derivatives toward Zinc Ion", 23$^{rd}$ Organic Synthesis Seminar for the young - for organic synthesis in the future, Dec. 9, 2003, listed as P42.

FLUORESCENT ZINC ION SENSOR

TECHNICAL FIELD

The present invention relates to a compound or salt thereof that can be used as a highly selective fluorescent zinc ion sensor.

BACKGROUND ART

Zinc ions play important roles in intracellular processes including enzyme catalysis, gene expression, apoptosis, neurotransmission and the like. Therefore, development of a zinc ion sensor is one of attractive fields for researchers of biological inorganic chemistry. Real time measurement of zinc ions and visualization of zinc ion distribution in living cells enable further elucidation of functions of zinc ions in bioprocesses in vivo.

As compounds that specifically bind to zinc ions, N,N,N', N'-tetrakis(2-pyridyl-methyl)ethylenediamine (TPEN) as a cell membrane-permeable zinc chelator is known (Helv. Chim. Acta, 50, 2330, 1967). Further, zinc ion sensors based on the photoinduced electron transfer (PET) mechanism have been extensively developed in recent years. In these sensors, a zinc ion binds to a heteroatom located near a fluorescent dye to inhibit PET, thereby a fluorescent property of the sensor molecule is switched on. As compounds wherein a zinc chelator moiety is introduced into a fluorescent fluorescein derivative, ZnAF-2 (J. Am. Chem. Soc., 122, 12399, 2000), Newport Green (the catalogue of Molecular Probes, Inc., "Handbook of Fluorescent Probes and Research Products" 8th edition, by Richard P. Haugland, pp. 805-817), Zinpyr-1 (J. Am. Chem. Soc., 122, 5644, 2000) and the like have been developed so far.

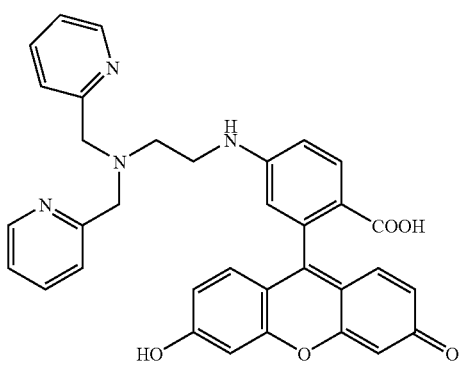

ZnAF-2

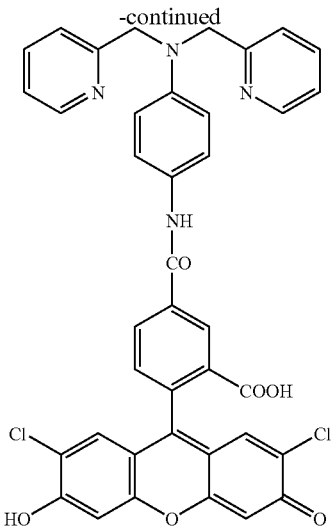

Newport Green

Zinpyr-1

Furthermore, various zinc ion sensors based on quinoline chromophores have also been developed. These sensors utilize fluorescence induced by complexation (Chelation Enhanced Fluorescence, CHEF), and light emission mechanism thereof has been studied in detail by using 2,6-bis (quinolinecarboxy)methylpyridine (P2Q)/zinc complex (J. Comput. Chem. Jpn., 2, pp.57-62, 2003). As zinc ion sensors based on this quinoline chromophores, TSQ (J. Neurosci. Methods, 20, 91, 1987), Zinquin (Biochem. J., 296, 403, 1993) and the like have already been practically used. However, since these compounds form both fluorescent 1:1 complex and 1:2 complex with zinc ions, quantitative analysis may sometimes become difficult when they are used for the measurement of zinc ions. Further, these zinc ion sensors, except for a few of them such as ZnAF-2, suffer from problems in that they have a high level of background fluorescence, and they are readily affected by pH in the physiological pH range, i.e., pH from 6 to 8. Moreover, these zinc ion sensors also have a problem in that multiple steps are required for their synthesis, and therefore, they cannot be manufactured in a large scale at low cost.

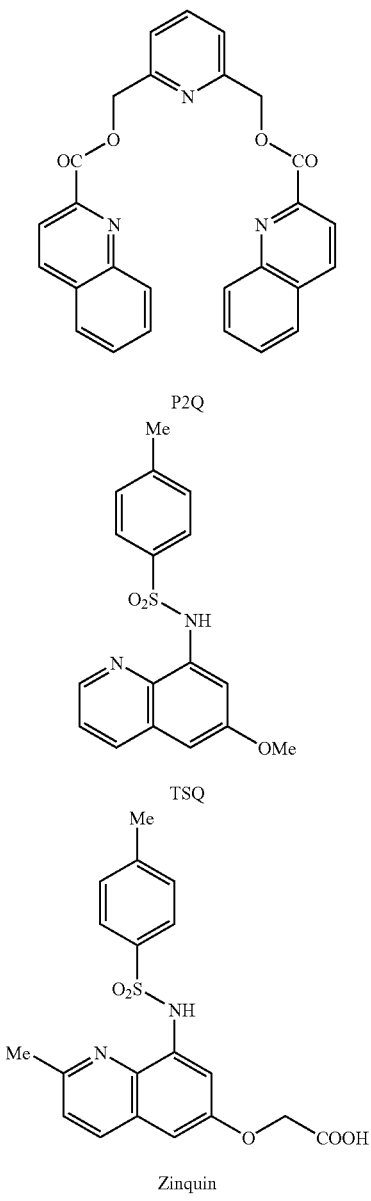

P2Q

TSQ

Zinquin

DISCLOSURE OF THE INVENTION

An object of the present invention is to provide a compound or salt thereof that can be used as a highly selective fluorescent zinc ion sensor. More specifically, the object of the present invention is to provide a compound or salt thereof that can specifically capture a zinc ion wherein the complex after the capture has a superior fluorescent characteristic. Further, another object of the present invention is to provide a compound that is not affected by physiological pH and can be used as a zinc ion sensor that can be produced at low cost.

The inventors of the present invention conducted various researches to solve the foregoing objects. As a result, they found that a compound obtained by replacing the pyridine ring of the cell membrane-permeable zinc chelator, TPEN, with a quinoline ring successfully formed a 1:1 complex with a zinc ion in the presence of zinc ions, and the resulting complex emitted intense fluorescence, and that the compound had superior advantageous characteristics as a fluorescent zinc ion sensor. The present invention was achieved on the basis of these findings.

The present invention thus provides a compound represented by the following general formula (I) or a salt thereof:

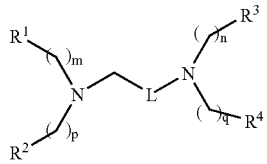

wherein $R^1$, $R^2$, $R^3$, and $R^4$ independently represent 2-quinolyl group which may be substituted, 1-isoquinolyl group which may be substituted, or 3-isoquinolyl group which may be substituted; m, n, p, and q independently represent 1 or 2; and L represents a single bond, or an alkylene group having 1 to 5 carbon atoms wherein said alkylene group may contain one or more heteroatoms in the main chain, and may have one or more substituents on the main chain.

From other aspects, the present invention also provides a fluorescent zinc ion sensor containing a compound represented by the aforementioned general formula (I) or a salt thereof; and a zinc complex formed with a compound represented by the aforementioned general formula (I) or a salt thereof and a zinc ion. This fluorescent zinc ion sensor can be used for the measurement of zinc ions in tissues or cells.

From further aspects, the present invention also provides a method for measuring zinc ions, which uses a compound represented by the aforementioned general formula (I) or a salt thereof as a fluorescent zinc ion sensor; a method for measuring zinc ions, which comprises (a) the step of reacting a compound represented by the aforementioned general formula (I) or a salt thereof and a zinc ion, and (b) the step of measuring fluorescence intensity of a zinc complex produced in the previous step; and use of a compound represented by the aforementioned general formula (I) or a salt thereof as a fluorescent zinc ion sensor.

Figure 1:
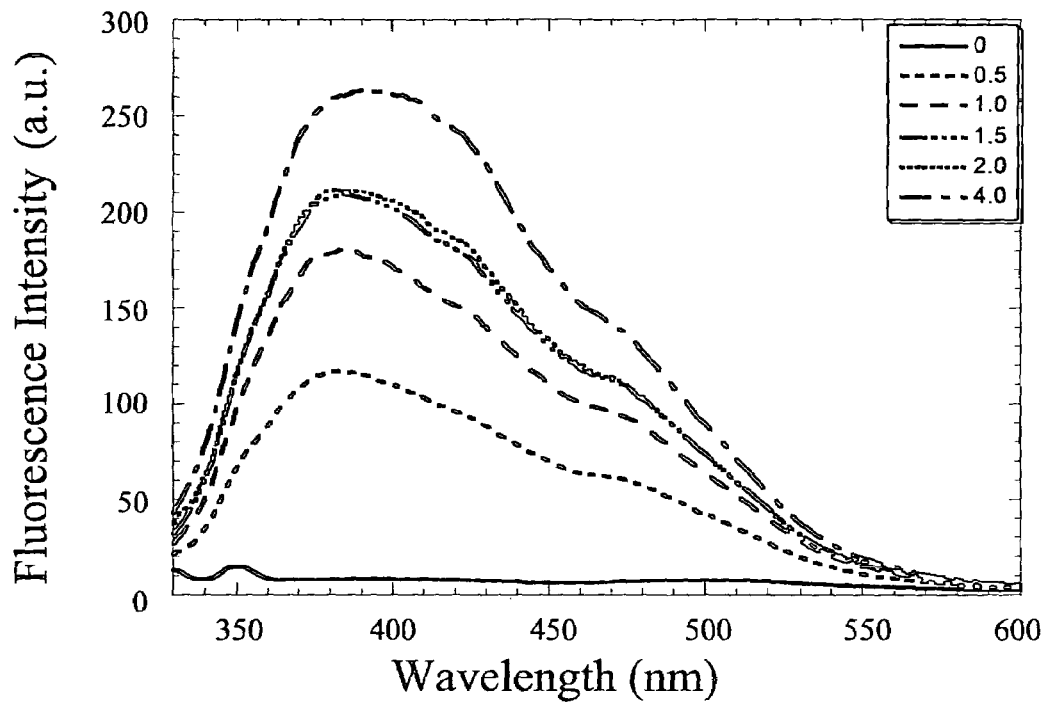
FIG. 1 shows fluorescent characteristics of the fluorescent zinc ion sensor (TQEN) of the present invention.

BEST MODE FOR CARRYING OUT THE INVENTION $R^1$, $R^2$, $R^3$, and $R^4$ independently represent 2-quinolyl group, 1-isoquinolyl group or 3-isoquinolyl group, and the 2-quinolyl group, 1-isoquinolyl group, and 3-isoquinolyl group may have one or more of any kinds of substituents at any positions. Each of $R^1$, $R^2$, $R^3$, and $R^4$ may be a different group. Alternatively, any two or more of them may be the same group.

When the 2-quinolyl group, 1-isoquinolyl group, or 3-isoquinolyl group is substituted, types and number of the substituents and the substituting positions are not particularly limited. Preferred substituting positions are one or more positions selected from the 5-, 6-, and 7-positions of 2-quinolyl group, 1-isoquinolyl group, or 3-isoquinolyl group. Although it is not intended to be bound by any specific theory, when one or more substituents are present in the aforementioned position(s), each of the substituents may not inhibit formation of a zinc complex of a compound represented by the general formula (I) with a zinc ion. The number of the substituents of the 2-quinolyl group, 1-isoquinolyl group, or 3-isoquinolyl group may preferably be about 1 to 3. Unsubstituted 2-quinolyl group, 1-isoquinolyl group, or 3-isoquinolyl group may also be preferred.

Examples of substituents that can be present on the 2-quinolyl group, 1-isoquinolyl group, or 3-isoquinolyl group include an alkyl group (the alkyl group may be a linear, branched, or cyclic alkyl, or a combination thereof, and has about 1 to 12 carbon atoms, preferably 1 to 8 carbon atoms, more preferably 1 to 6 carbon atoms, which also applies to an alkyl moiety of other substituents having the alkyl moiety, e.g., alkoxy group and the like), an alkoxy group, hydroxyl group, an alkylcarbonyloxy group, an alkyloxycarbonylalkyloxy group, carboxyl group, an alkyloxycarbonyl group, succimidyloxycarbonyl group, an alkylcarbonyloxymethyloxycarbonyl group, amino group, an alkylamino group, a halogen group (the halogen atom may be any of fluorine atom, chlorine atom, bromine atom, and iodine atom), thiol group, an alkylthio group, a halogenated alkyl group, nitro group, sulfo group and an ester thereof, phosphono group and an ester thereof and the like. However, the substituents are not limited to these examples. One or more substituents may further be present on the aforementioned substituents.

In the general formula (I), m, n, p, and q independently represent 1 or 2. When m, n, p, or q is 1, methylene group is meant to be present. When m, n, p, or q is 2, ethylene group is meant to be present. It is preferred that each of m, n, p, and q represents 1. Symbol "L" represents a single bond, or an alkylene group having 1 to 5 carbon atoms. The alkylene group may contain one or more heteroatoms in the main chain or may have one or more substituents on the main chain. In the present specification, the term "heteroatom" means a non-metal atom except carbon atom, such as nitrogen atom, oxygen atom or sulfur atom. The alkylene group may have a branched chain, however, a linear alkylene group is preferred. The term "main chain" means an atomic chain in "L," with minimum number of atoms, that connect each of the nitrogen atom and the carbon atom bound at each end of L. Examples of L containing a heteroatom in the main chain include —$CH_2$—O—$CH_2$—, —$CH_2$—S—$CH_2$—, —$C_2(CH_3)$—$C_2$—O—$CH_2$—, —$CH_2$—$CH_2$—O— and the like. However, L is not limited to these examples. The number, substituting positions ,and types of substituents that can be present on the main chain of L are not particularly limited. As substituents, such as those exemplified above as substituents that can be present on the 2-quinolyl group, 1-isoquinolyl group, or 3-isoquinolyl group can be used.

Preferred examples of the compounds represented by the general formula (I) will be mentioned below. However, the compounds of the present invention are not limited to these examples.

Among the compounds exemplified, the compounds where methoxy groups substitute on the quinoline ring have a property of a shift of an excitation wavelength to the side of longer wavelength, and therefore, they are highly useful for measurement of zinc ions in vivo because cell injury by the excitation light can be reduced.

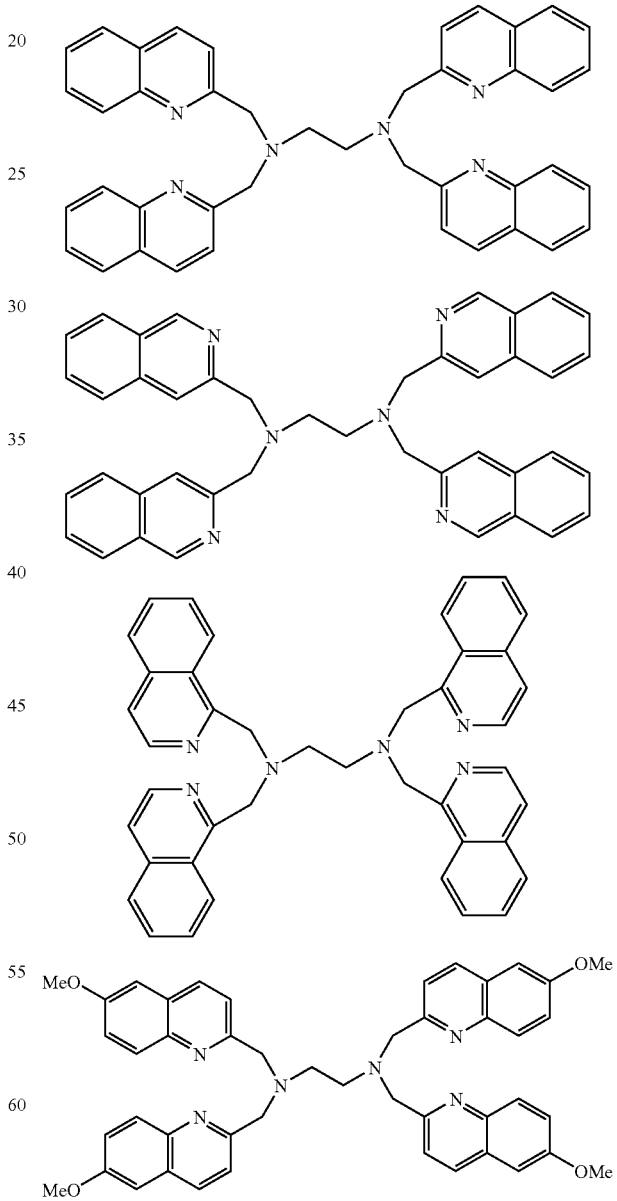

-continued

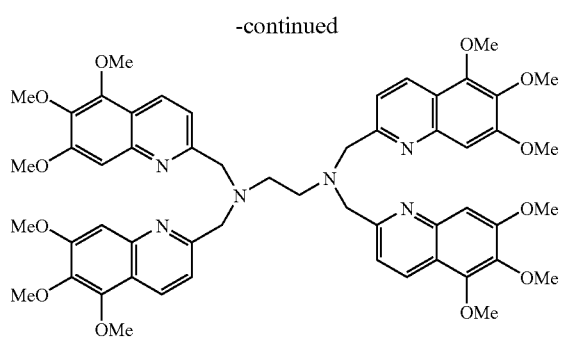

The compounds of the present invention represented by the aforementioned general formula (I) can exist as acid addition salts, and can also exist as base addition salts depending on type of substituents. Examples of the acid addition salts include mineral acid salts such as hydrochlorides, sulfates, and nitrates, and organic acid salts such as methanesulfonates, p-toluenesulfonates, oxalates, citrates, and tartrates and the like. Base addition salts are formed, for example, when a substituent of carboxyl group or the like exists, and examples thereof include metal salts such as sodium salts, potassium salts, calcium salts, and magnesium salts, ammonium salts, and organic amine salts such as triethylamine salts and the like. In addition to these examples, they may form salts with an amino acid such as glycine. The compounds of the present invention or salts thereof may also exist as hydrates or solvates, and any of these substances falls within the scope of the present invention.

The compounds of the present invention represented by the aforementioned general formula (I) may have one or more asymmetric carbons depending on type of substituent. In addition to stereoisomers such as optically active substances based on one or more asymmetric carbons or diastereoisomers based on two or more asymmetric carbons, any of arbitrary mixtures of stereoisomers, racemates and the like also fall within the scope of the present invention.

Among the compounds of the present invention represented by the general formula (I), compounds wherein $R^1$, $R^2$, $R^3$, and $R^4$ represent 2-quinolyl group, m, n, p and q represent 1, and L represents methylene group can be produced by one step, for example, by reacting 2-chloromethylquinoline and ethylenediamine. Details of this synthetic method will be described in the examples. Those skilled in the art can also readily synthesize other compounds that fall within the scope of the general formula (I) by referring to the methods described in the examples and by suitably choosing reaction raw materials, reaction conditions, reaction reagents and the like, and further adding modifications or alterations to these methods as required.

The compounds of the present invention represented by the aforementioned general formula (I) or salts thereof are useful as fluorescent zinc ion sensors. Although the compounds of the present invention represented by the aforementioned general formula (I) or salts thereof themselves do not have a property of emitting intense fluorescence, they come to emit intense fluorescence when they capture zinc ions to form zinc complexes. The aforementioned compounds or salts thereof have characteristic features that they can specifically capture zinc ions and the formation of the complex is extremely fast. The compounds of the present invention also have characteristic features that they have substantially no background fluorescence, and the zinc complexes formed are hardly affected by pH within neutral range (pH 6 to 8) and emit stable and intense fluorescence. Therefore, the compounds of the present invention represented by the aforementioned general formula (I) or salts thereof are extremely useful as fluorescent zinc ion sensors for the measurement of zinc ions in living cells and living tissues under physiological condition. The term "measurement" used in the present specification should be construed in the broadest sense including quantification and qualification.

Methods for using the fluorescent zinc ion sensors of the present invention are not particularly limited, and they can be used in the same manner as those for known zinc ion sensors. Ordinarily, a single kind of substances selected from the group consisting of the compounds represented by the aforementioned general formula (I) and salts thereof may be dissolved in an aqueous medium such as physiological saline or buffer, a mixture of water-miscible organic solvent such as ethanol, acetone, ethylene glycol, dimethyl sulfoxide, or dimethylformamide and the aqueous medium or the like, and the resulting solution may be added to the suitable buffer containing cells or tissue to measure fluorescence spectra. The fluorescent zinc ion sensor of the present invention may be combined with suitable additives and used in the form of compositions. For example, they can be combined with additives such as buffering agent, solubilizing agent, pH regulator and the like.

EXAMPLES

The present invention will be explained more specifically with reference to the following examples. However, the scope of the present invention is not limited to these examples.

Example 1

Synthesis of N,N,N',N'-tetrakis(2-quinolylmethyl) ethylenediamine (TQEN)

A mixture of 2-chloromethylquinoline hydrochloride (1.07 g, 5 mmol), ethylenediamine (75.0 mg 1.25 mmol), potassium carbonate (2.07 g, 15 mmol) and acetonitrile (10 mL) was refluxed by heating for 48 hours. The solvent was evaporated under reduced pressure, and then the residue was separated by phase separation using chloroform and water. The organic layer was dried, and the solvent was evaporated. The residue was washed with acetone to obtain the objective compound as white powder (0.70 g, 89%).

mp 196 to 198° C. $^1$H NMR (CDCl$_3$) δ (ppm): 2.89 (s, 4H), 3.96 (s, 8H), 7.49-7.54 (m, 8H), 7.66-7.71 (q, 8H), 7.87 (d, 4H), 7.99 (d, 4H) $^{13}$C NMR (CDCl$_3$) δ (ppm): 52.58, 61.56, 120.85, 125.95, 127.16, 127.34, 128.88, 129.23, 136.08, 147.40, 160.29 ESI-MS calcd. for $C_{42}H_{37}N_6$ ([M+H]$^+$): 625.3074; Found: 625.3070 Anal. calcd. for $C_{42}H_{36}N_6$: C, 80.61; H, 5.96; N, 13.43, Found: C, 80.69; H, 5.92; N, 13.41

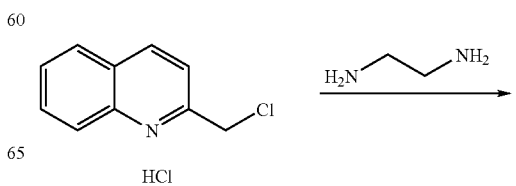

-continued

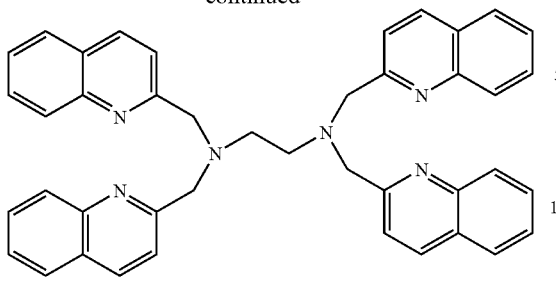

Example 2

Synthesis of [Zn(TQEN)](ClO$_4$)$_2$

A mixture of TQEN (0.31 g, 0.50 mmol) and zinc perchlorate (0.18 g, 0.49 mmol) was stirred in acetonitrile at room temperature for 4 days. A small amount of unnecessary substances were removed by filtration, and then the solvent was evaporated under reduced pressure. The obtained residue was recrystallized from acetonitrile/ether to obtain a single crystal suitable for X-ray crystal structure analysis.

$^1$H NMR (CD$_3$CN) δ (ppm): 3.18 (s, 4H), 4.1 (br., 4H), 4.43 (d, 4H), 7.3 (br., 4H), 7.46 (d, 4H), 7.5-7.7 (m, 4H), 8.07 (d, 4H), 8.56 (d, 4H) $^{13}$C NMR (CD$_3$CN) δ (ppm): 57.00, 63.18, 123.17, 126.45, 129.19, 130.45, 130.79, 132.83, 142.94, 145.72, 160.78 ESI-MS calcd. for C$_{42}$H$_{36}$N$_6$ZnClO$_4$ ([Zn(TQEN)]ClO$_4$): 787.1773; Found: 787.1766 Anal. calcd. for C$_{42}$H$_{38}$N$_6$ZnCl$_2$O$_9$([Zn(TQEN)](ClO$_4$)$_2$.H$_2$O): C, 55.61; H, 4.22; N, 9.26, Found: C, 55.85; H, 4.18; N, 9.35

Example 3

Synthesis of 6-methoxy-2-bromomethylquinoline

A mixture of 6-methoxy-2-methylquinoline (999 mg, 5.77 mmol), NBS (1.03 g, 5.77 mmol), AIBN (153 mg) and chlorobenzene (10 mL) was stirred at 120° C. for 2 hours, then added with AIBN (153 mg) again and further stirred for 4 hours with heating. The solvent was evaporated under reduced pressure, and then the residue was extracted with ether. The solvent was evaporated, and the residue was recrystallized from ethanol to obtain 6-methoxy-2-bromomethylquinoline as white powder (yield: 400 mg, 1.59 mmol, 28%).

$^1$H NMR (CDCl$_3$) δ (ppm): 3.94 (s, 3H), 4.70 (s, 2H), 7.08 (d, 1H), 7.39 (q, 1H), 7.53 (d, 1H), 7.97 (d, 1H), 8.07 (d, 1H) $^{13}$C NMR (CDCl$_3$) δ (ppm): 34.70, 55.69, 105.22, 121.74, 122.94, 128.68, 130.95, 136.25, 143.87, 154.62, 158.52

Example 4

Synthesis of N,N,N',N'-tetrakis(6-methoxy-2-quinolylmethyl)-ethylenediamine (6OMeTQEN)

A mixture of 6-methoxy-2-bromomethylquinoline (0.076 g, 0.302 mmol), ethylenediamine (5 μL, 0.0755 mmol), potassium carbonate (0.125 g, 0.904 mmol) and acetonitrile (6 mL) was refluxed by heating for 14 hours. The solvent was evaporated under reduced pressure, and then the residue was separated by phase separation using chloroform and water. The organic layer was dried, and then the solvent was evaporated. The residue was washed with ethanol to obtain the objective compound as white powder (yield: 18.7 mg, 33%).

mp 168 to 170° C. $^1$H NMR (CDCl$_3$) δ (ppm): 2.84 (s, 4H), 3.90 (d, 20H), 6.94 (d, 4H), 7.30 (q, 4H), 7.48 (d, 4H), 7.78 (d, 4H), 7.88 (d, 4H) $^{13}$C NMR (CDCl$_3$) δ (ppm): 52.78, 55.26, 55.50, 61.55, 105.05, 105.34, 121.35, 121.70, 121.81, 128.20, 130.21, 130.50, 134.87, 135.15, 143.51, 157.49, 157.94 ESI-MS calcd. for C$_{46}$H$_{45}$N$_6$O$_4$ ([M+H]$^+$): 745.35; Found: 745.25

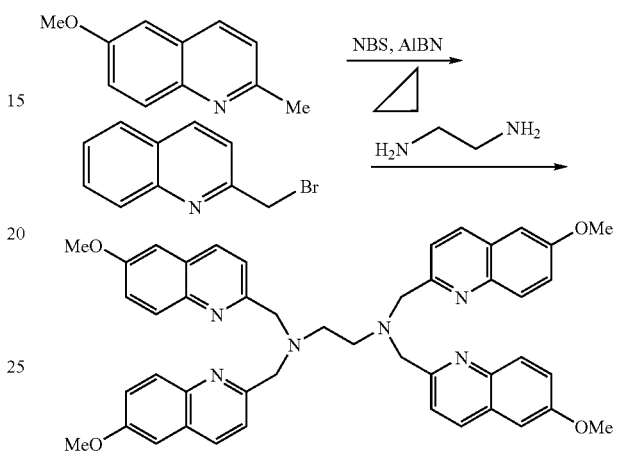

Test Example 1

Figure 2:
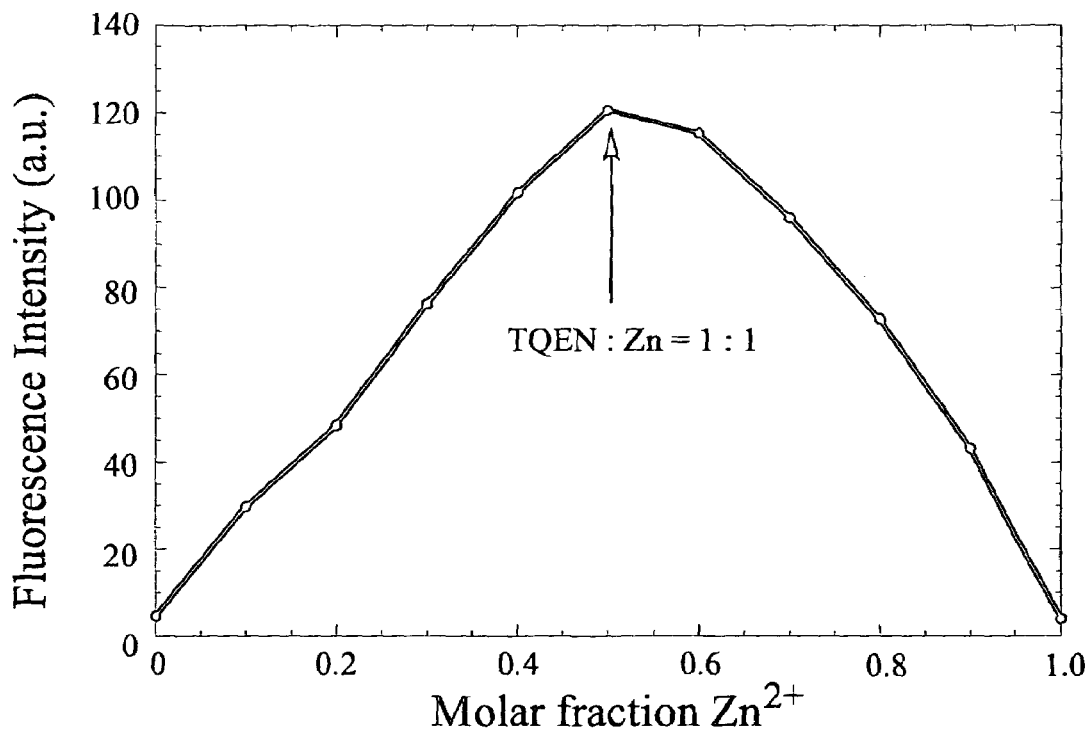
FIG. 2 shows results of job plot analyses of complex formation of TQEN with zinc ions.

When TQEN was irradiated with light of 317 nm in dimethylformamide (DMF) or a water-containing DMF solution (DMF:water=1:1), substantially no fluorescence was emitted. Whilst, fluorescence from TQEN was observed when zinc ions were added (fluorescence of 383 nm, FIG. 1). Further, job plot analyses revealed that TQEN formed a complex with 1 equivalent of zinc ions (FIG. 2).

Test Example 2

Figure 3:
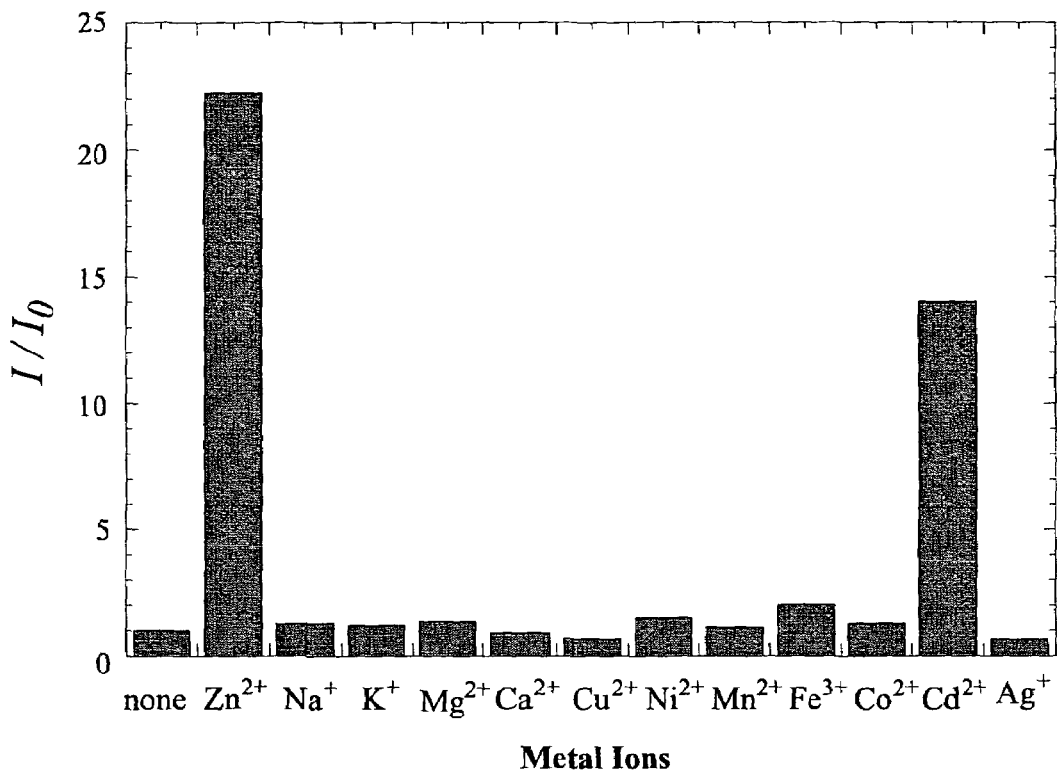
FIG. 3 shows fluorescent responses of TQEN in the presence of various metal ions.

Fluorescent responses of TQEN in the presence of various metal ions are shown in FIG. 3. TQEN emitted intense fluorescence in the presence of zinc ions or cadmium ions (about 60% of the fluorescence intensity obtained in the presence of zinc ions). Whilst, other metal ions gave almost no effect on the fluorescence of TQEN. None of sodium, potassium, magnesium, calcium, nickel, and manganese ions affected the fluorescence of the TQEN/zinc complex. However, 1 equivalent of copper, cobalt, cadmium, or silver ions and excess amount of iron ions inhibited fluorescence emission by TQEN with zinc, so it is possible that these metal ions form stronger complexes than zinc ions.

Test Example 3

Figure 4:
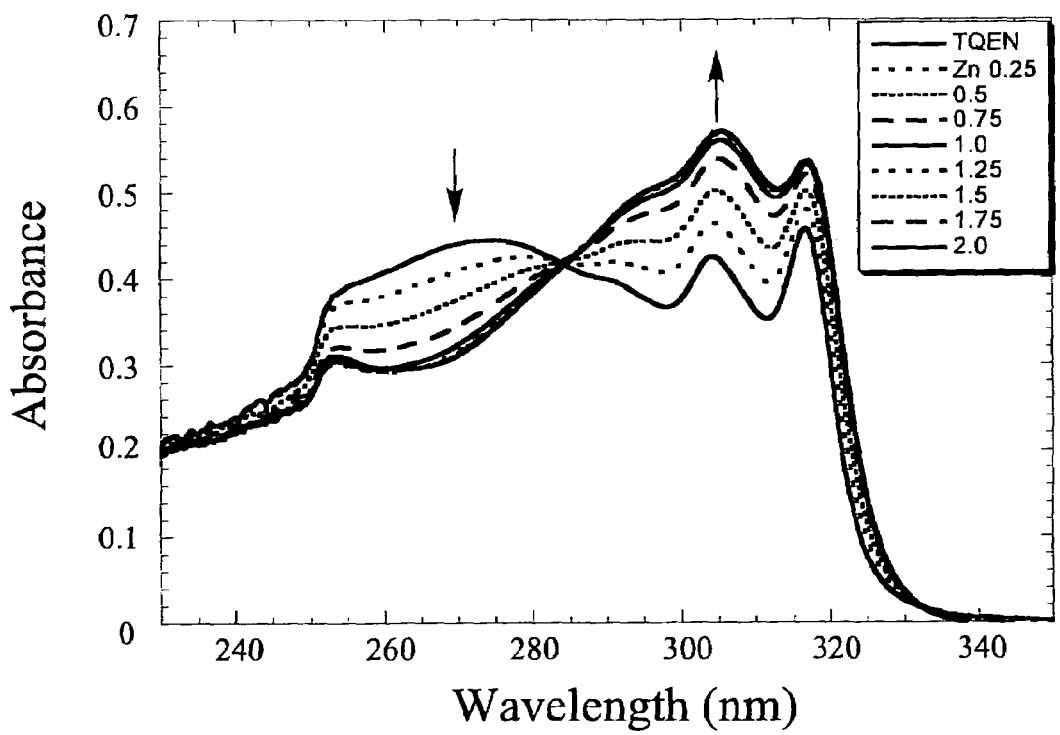
FIG. 4 shows results of titration of TQEN with zinc ions where changes were monitored by ultraviolet and visible absorption spectra.

TQEN was titrated with zinc ions, and changes of ultraviolet and visible absorption spectra were monitored. The changes of absorption had an isosbestic point and stopped when 1 equivalent of zinc ions were added (FIG. 4). The results suggest that a TQEN complex containing more than 1 equivalent of zinc ions has the same absorbance as that of the 1:1 TQEN/zinc complex. In a competition experiment, metals in the former class of ions (sodium, potassium and the like) gave no change in absorption spectra of TQEN, whilst those of the latter class of ions (copper, cobalt and the like) induced the same spectral changes as those induced by zinc.

Test Example 4

Figure 5:
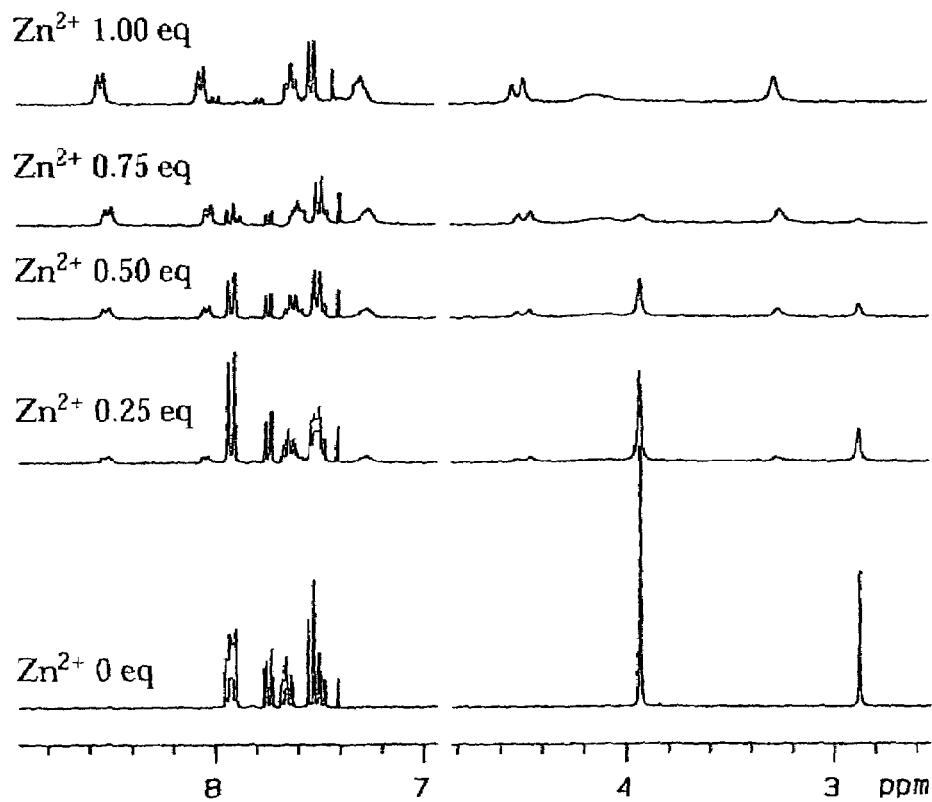
FIG. 5 shows results of titration of TQEN with zinc ions by means of NMR.

When TQEN was titrated with zinc and monitored by NMR, different peaks of TQEN and the TQEN/zinc complex were observed. The result suggests that an exchange rate between TQEN and TQEN bound with zinc is slower than the time scale of NMR (FIG. 5). In the zinc complex, the hydrogen atom at the benzyl position was observed as an AB quartet due to restricted degree of freedom of the conformation of the hydrogen atom in the complex. Further, in a competition experiment in the presence of 1 equivalent of TPEN, fluorescence from the TQEN/zinc complex completely disappeared. The result suggests that the zinc ion in the TQEN/zinc complex is completely removed by the stronger zinc ligand, TPEN. The zinc ion was not completely removed from the TQEN/zinc complex in an experiment using 1 equivalent of EGTA (ethylene glycol-bis(2-aminomethyl)-N,N,N',N'-tetraacetic acid, $K_{Zn}$=not over $10^9$ M), and only about 40% of fluorescence of the TQEN/zinc complex was quenched by EGTA in DMF-containing aqueous solution.

Test Example 5

Figure 6:
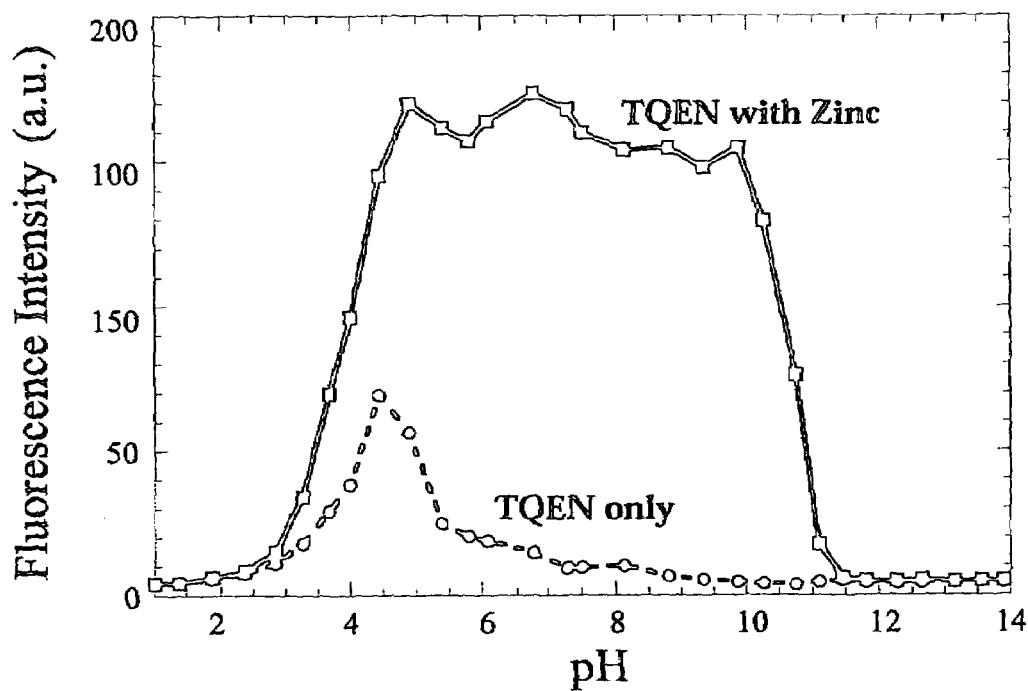
FIG. 6 shows influence of pH on fluorescence intensity of a TQEN/zinc complex.

Influences by pH on fluorescent intensity of the TQEN/zinc complex was shown in FIG. 6. Stable and intense fluorescent intensities were obtained within the range of pH 4 to 10, which clearly indicate that the TQEN/zinc complex can be used as a fluorescent zinc ion sensor in a broad pH range.

Test Example 6

A single crystal of $[Zn(TQEN)](ClO_4)_2 \cdot 2.5CH_3CN$ was coated with paraffin oil and mounted on glass fibers. Measurements were performed at 173 K. For the measurements, monochromated MoKa of 50 kV/40 mA was used as a radiation source, and Rigaku Mercury CCD Detector was used. Substantially no decrease in peaks was observed during the measurements. The data were analyzed on PC by using CrystalClear Software (Rigaku). The structure was optimized by the direct method (SIR-92) using the least square method with respect to $F^2$. Hydrogen atoms were considered as a riding model. The crystallographic data are summarized in Table 1. Major bond distances and angles are summarized in Table 2.

TABLE 1

| Compounds | $Zn(TQEN)](ClO_4)_2 \cdot 2.5CH_3CN$ |
|---|---|
| Formula | $C_{47}H_{43.5}Cl_2N_{8.5}O_8Zn$ |
| FW | 991.70 |
| Space group | P-1 |
| a, Å | 12.581(3) |
| b, Å | 19.334(2) |
| c, Å | 21.051(5) |
| α, deg | 75.849(9) |
| β, deg | 72.6470(13) |
| γ, deg | 71.045(11) |
| V, Å$^3$ | 4559.9(16) |
| Z | 4 |
| $D_{calc}$, g cm$^{-3}$ | 1.444 |
| μ, cm$^{-1}$ | 7.20 |
| $2\theta_{max}$, deg | 55.0 |
| temp, K | 173 |
| no. reflns measd | 19595 |
| no. reflns used | 19595 |
| no. of params | 1275 |
| final R1 (I > 2θ(I)) | 0.078 |
| wR2 (all data) | 0.207 |
| GOF | 1.22 |

$R1 = \Sigma ||F_o| - |F_c||/\Sigma|F_o|.$
$wR2 = [\Sigma w[(F_o^2 - F_c^2)^2]/\Sigma[w(F_o^2)^2]]^{1/2}.$

TABLE 2

| | $Zn(TQEN)](ClO_4)_2$ |
|---|---|
| Zn—N(1) | 2.149(3), 2.147(3) |
| Zn—N(2) | 2.169(3), 2.168(3) |
| Zn—N(3) | 2.149(3), 2.150(3) |
| Zn—N(4) | 2.393(3), 2.393(3) |
| Zn—N(5) | 2.130(3), 2.131(3) |
| Zn—N(6) | 2.369(3), 2.370(3) |
| N(1)-Zn—N(2) | 82.15(11), 82.15(11) |
| N(1)-Zn—N(3) | 76.15(11), 76.18(11) |
| N(1)-Zn—N(4) | 77.98(10), 78.03(10) |
| N(1)-Zn—N(5) | 159.48(10), 159.48(11) |
| N(1)-Zn—N(6) | 92.23(10), 92.21(10) |
| N(2)-Zn—N(3) | 157.67(11), 157.65(11) |
| N(2)-Zn—N(4) | 90.64(10), 90.74(10) |
| N(2)-Zn—N(5) | 77.72(10), 77.75(10) |
| N(2)-Zn—N(6) | 77.94(10), 77.70(10) |
| N(3)-Zn—N(4) | 89.99(10), 90.04(10) |
| N(3)-Zn—N(5) | 124.24(10), 124.21(10) |
| N(3)-Zn—N(6) | 97.48(10), 97.58(10) |
| N(4)-Zn—N(5) | 98.14(9), 98.03(10) |
| N(4)-Zn—N(6) | 165.96(10), 165.87(10) |
| N(5)-Zn—N(6) | 87.49(10), 87.53(10) |

Figure 7:
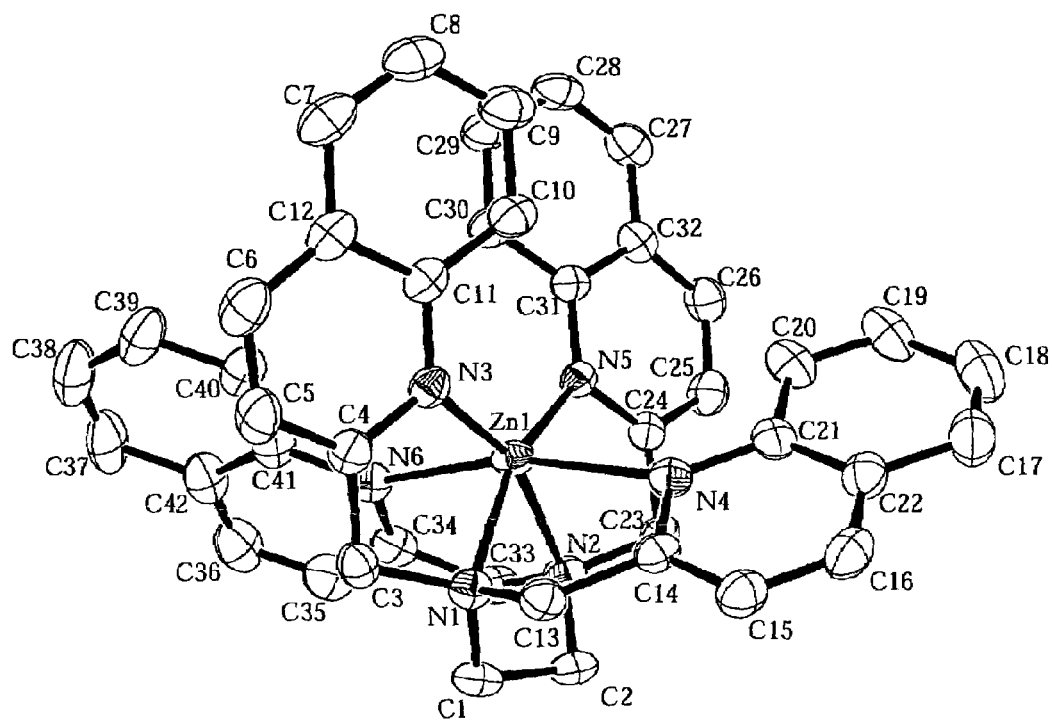
FIG. 7 shows a result of X-ray structural analysis of a TQEN/zinc complex.

The TQEN/zinc complex exists as two kinds of crystallographically independent molecules, one of which is shown in FIG. 7. TQEN binds to a zinc ion by means of 6 nitrogen atoms and provides an irregular octahedral coordination environment and twisted structure surrounding the zinc ion. All the 4 quinoline rings in the TQEN/zinc complex are in propeller-like positions due to steric hindrance between two quinoline rings (twisting angle: 21 degrees). This characteristic bonding scheme is considered to provide the desirable fluorescence feature of the TQEN/zinc complex.

Test Example 7

Figure 8:
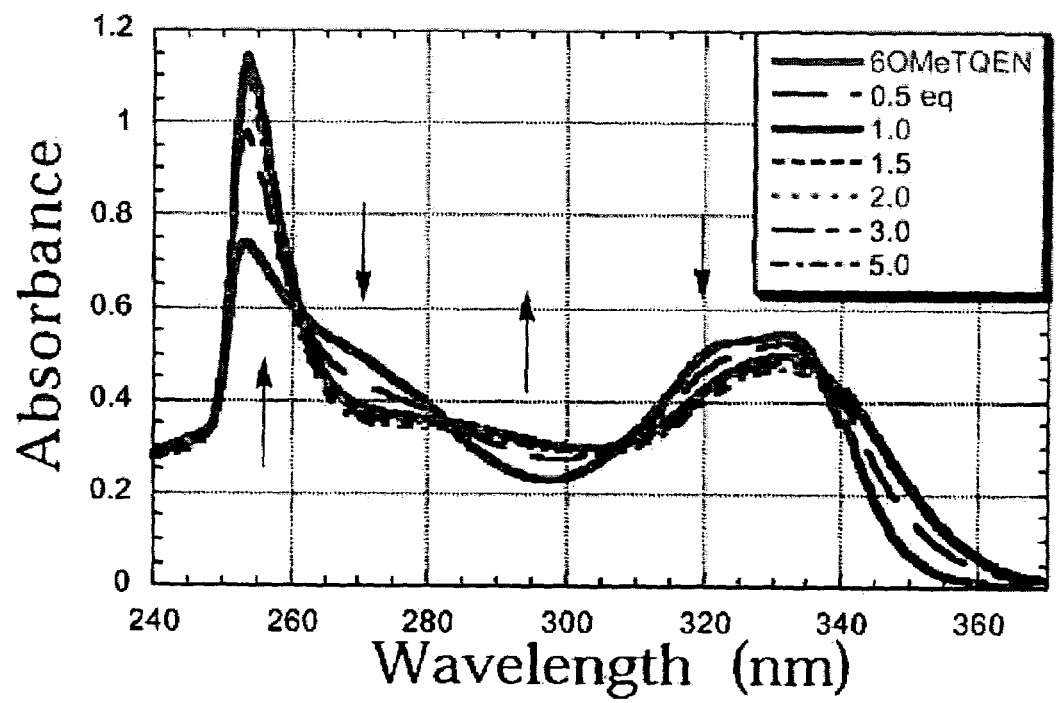
FIG. 8 shows results of titration of 6OMeTQEN with zinc ions where changes in absorption were monitored by ultraviolet and visible absorption spectra.

In the same manner as in Test Example 3, solution of 6OMeTQEN (concentration of 6OMeTQEN: 34 μM) in water-containing DMF (DMF:water=1:1) was titrated with zinc ions (0 to 68 μM), and changes in absorption were monitored by measuring ultraviolet and visible absorption spectra (FIG. 8). As a result, it was confirmed that absorption wavelength was extended to around 350 nm, which is longer by about 20 nm than that of TQEN.

Test Example 8

Figure 9:
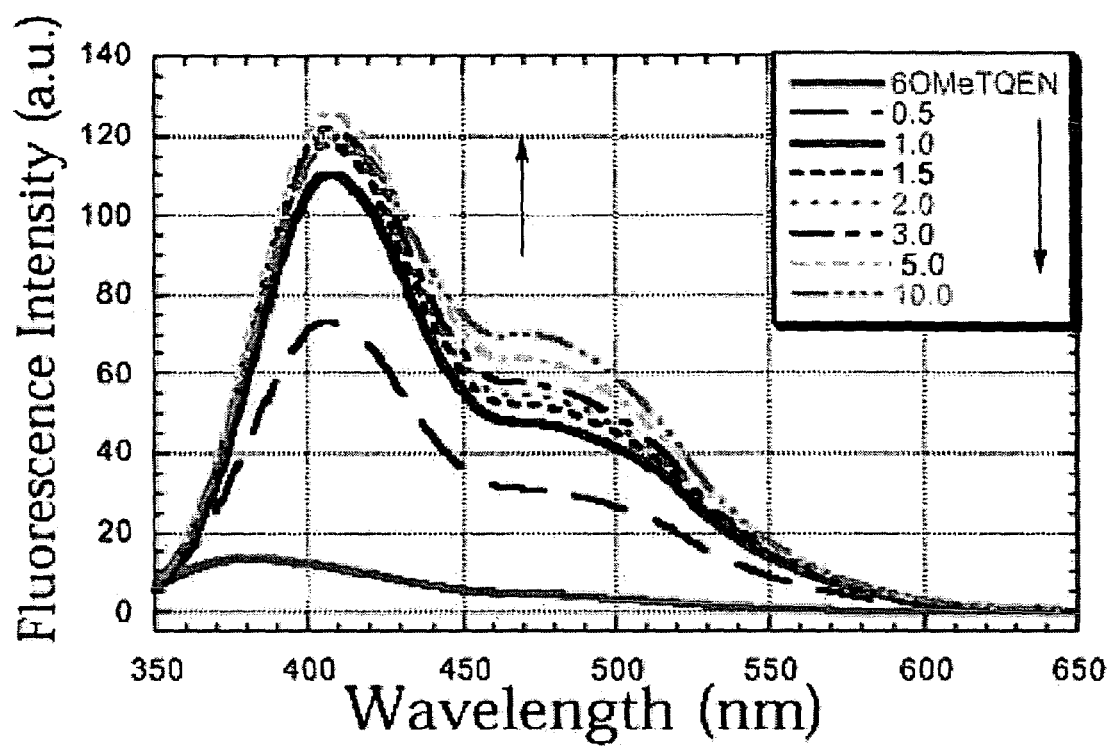
FIG. 9 shows fluorescent characteristics of the fluorescent zinc ion sensor (6OMeTQEN) of the present invention.

When 6OMeTQEN was irradiated with light having a wavelength of 340 nm, which was longer than the excitation wavelength (317 nm) of TQEN, in a water-containing DMF solution (DMF:water=1:1, concentration of 6OMeTQEN: 34 μM) in the same manner as that in Test Example 1, substantially no fluorescence was emitted. Whilst an increase in fluorescence emitted from 6OMeTQEN was observed when zinc ions (0 to 68 μM) were added (fluorescence of 410 nm, FIG. 9). These results suggest that 6OMeTQEN enables measurement of zinc ion concentrations using excitation light having a longer wavelength compared with TQEN, thereby successful reduction of cell injury due to excitation light is achievable when zinc ions in vivo, for example, are measured.

INDUSTRIAL APPLICABILITY

The compounds represented by the aforementioned general formula (I) or salts thereof can be synthesized by one step in high yield by reacting ethylenediamine with 2-chloromethylquinoline or the like, and are characterized by successfully achieving specific capture of a zinc ion. Further, the complexes formed by the capture of zinc ions have superior fluorescent characteristics and are not affected by a physiological pH. Therefore, the compounds represented by the aforementioned general formula (I) or salts thereof are useful as fluorescent zinc ion sensors.

What is claimed is:

1. A compound represented by the following general formula (I) or a salt thereof:

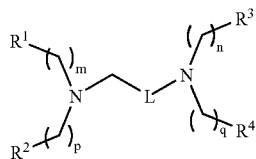

wherein $R^1$, $R^2$, $R^3$, and $R^4$ independently represent 2-quinolyl group which may be substituted with an alkoxy, 1-isoquinolyl group which may be substituted with an alkoxy, or 3-isoquinolyl group which may be substituted with an alkoxy; m, n, p, and q independently represent 1 or 2; and L represents a single bond, or an alkylene group having 1 to 5 carbon atoms.

2. The compound or a salt thereof according to claim 1, wherein $R^1$, $R^2$, $R^3$, and $R^4$ represent 2-quinolyl group which may be substituted with an alkoxy; m, n, p, and q represent 1; and L represents methylene group.

3. A fluorescent zinc ion sensor, which comprises the compound represented by the general formula (I) or a salt thereof according to claim 1.

4. A zinc complex formed by the compound represented by the general formula (I) or a salt thereof according to claim 1 and a zinc ion.

5. A method for measuring zinc ions, which comprises:
(a) reacting a compound represented by the general formula (I) or a salt thereof according to claim 1 and a zinc ion to produce a zinc complex, and
(b) measuring fluorescent intensity of the zinc complex.

6. A fluorescent zinc ion sensor, which comprises the compound represented by the general formula (I) or a salt thereof according to claim 2.

7. A zinc complex formed by the compound represented by the general formula (I) or a salt thereof according to claim 2 and a zinc ion.

8. A method for measuring zinc ions, which comprises:
(a) reacting a compound represented by the general formula (I) or a salt thereof according to claim 2 and a zinc ion to produce a zinc complex, and
(b) measuring fluorescent intensity of the zinc complex.

* * * * *

UNITED STATES PATENT AND TRADEMARK OFFICE
CERTIFICATE OF CORRECTION

PATENT NO. : 7,541,467 B2
APPLICATION NO. : 10/902432
DATED : June 2, 2009
INVENTOR(S) : Shigenobu Yano et al.

It is certified that error appears in the above-identified patent and that said Letters Patent is hereby corrected as shown below:

On the Title page, References Cited (56), Other Publications (Page 3, Left Column, Line 17) of the printed patent, "pp 477-382 (2000)" should be --pp 477-482 (2000)--.

Signed and Sealed this

Fifth Day of January, 2010

David J. Kappos
*Director of the United States Patent and Trademark Office*